(12) United States Patent
Scholl et al.

(10) Patent No.: US 6,895,337 B1
(45) Date of Patent: May 17, 2005

(54) METHOD OF IDENTIFYING GENOMIC REARRANGEMENTS

(75) Inventors: Thomas Scholl, Salt Lake City, UT (US); Dmitry Pruss, Salt Lake City, UT (US); Brant C. Hendrickson, South Jordan, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 309 days.

(21) Appl. No.: 10/272,609

(22) Filed: Oct. 15, 2002

Related U.S. Application Data
(60) Provisional application No. 60/328,873, filed on Oct. 12, 2001.

(51) Int. Cl.$^7$ .......................... G06F 19/00; G11C 17/00; G05B 15/00

(52) U.S. Cl. .............................. 702/20; 365/94; 700/1

(58) Field of Search ........................... 702/20; 365/94; 700/1

(56) References Cited

PUBLICATIONS

Adkins comparison of the accuracy of methods of computational haplotype inference using a large empirical dataset. BMC Genetics vol. 5, article 22 (2004).*
Clark, Andrew G., et al., "Inference of Haplotypes from PCR–amplified Samples of Diploid Populations", *Mol. Biol. Evol.*, 1990; 7(2):111–122.
Excoffier, Laurent, et al., "Maximum–Likelihood Estimation of Molecular Haplotype Frequencies in a Diploid Population", *Mol. Biol. Evol.*, 1995; 12(5):921–927.
Swensen, Jeff, et al., "Identification of a 14 kb deletion involving the promoter region of BRCA1 in a breast cancer family", *Human Molecular Genetics*, 1997; 6(9):1513–1517.
Puget, Nadine, et al., "A 1–kb Alu–mediated Germ–Line Deletion Removing BRCA1 Exon 17", *Cancer Research*, Mar. 1, 1997; 57:828–831.
Shattuck–Eidens, Donna, et al., "BRCA1 Sequence Analysis in Women at High Risk for Susceptibility Mutations", *JAMA*, Oct. 15, 1997; 278(15):1242–1250.
Petrij–Bosch, Anne, et al.,. "BRCA1 genomic deletions are major founder mutations in Dutch breast cancer patients", *Nature Genetics*, Nov. 1997; 17:341–345.
Nordling, Margareta, et al., "A Large Deletion Disrupts the Exon 3 Transcription Activation Domain of the BRCA2 Gene in a Breast/Ovarian Cancer Family", *Cancer Res.*, Apr. 1, 1998; 58(7):1372–1375.
Puget, Nadine, et al., "An Alu–Mediated 6–kb Duplication in the BRCA1 Gene: A New Founder Mutation?", *Am. J. Hum. Genet.*, 1999; 64:300–302.

Puget, Nadine, et al., "Screening for Germ–Line Rearrangements and Regulatory Mutations in BRCA1 Led to the Identification of Four New Deletions", *Cancer Res.*, Jan. 15, 1999, 59:455–461.
Montagna, Marco, et al., "Identification of a 3 kb Alu–mediated BRCA1 gene rearrangement in two breast/ovarian cancer families", *Oncogene*, Jul. 15, 1999; 18(28):4160–4165.
BRCA1 Exon 13 Duplication Screening Group, "The Exon 13 Duplication in the BRCA1 Gene Is a Founder Mutation Present in Geographically Diverse Populations", *Am. J. Hum. Genet.*, 2000; 67:207–212.
Fallin, Daniele, et al., "Accuracy Of Haplotype Frequency Esitmation For Biallelic Loci, Via The Expectation–Maximization Algorithm For Unphased Diploid Genotype Data", *Am. J. Hum. Genet.*, 2000; 67:947–959.
Robinson, M.D., et al., "Exon Deletions and Duplications in BRCA1 Detected by Semiquantitative PCR", *Genetic Testing*, 2000; 4(1):49–54.
Unger, Meredith A., et al., "Screening for Genomic Rearrangements in Families with Breast and Ovarian Cancer Identifies BRCA1 Mutations Previously Missed by Conformation–Sensitive Gel Electrophoresis or Sequencing", *Am. J. Hum. Genet.*, 2000; 67:841–850.
Stephens, Matthew, et al., "A New Statistical Method for Haplotype Reconstruction from Population Data", *Am. J. Hum. Genet.*, 2001; 68:978–989.
Gad, Sophie, et al., "Identification of a large rearrangement of the BRCA1 gene using colour bar code on combed DNA in an American breast/ovarian cancer family previously studied by direct sequencing", *J. Med. Genet.*, Jun. 2001; 38(6):388–392.
Daly, Mark J., et al., "High–Resolution haplotype structure in the human genome", *Nature Genetics*, Oct. 2001; 29:229–232.

(Continued)

Primary Examiner—John S. Brusca
(74) Attorney, Agent, or Firm—Jay Z. Zhang; Jonathan A. Baker; Myriad IP Dept.

(57) ABSTRACT

Methods, computer program products and systems are provided for detecting large genomic rearrangements based on unphased genotype data obtained using common genotyping techniques that do not differentiate different alleles. In the method, unphased genotypes at a plurality of nucleotide variant markers of a particular gene in a diploid subject are compared with a canonical haplotype collection of the gene for a heterogeneous subject population. If the unphased genotypes cannot be reduced to a pair of canonical haplotypes within the canonical haplotype collection, it would indicate an increased likelihood that an allele of the gene in the diploid subject harbors a genomic rearrangement.

33 Claims, 2 Drawing Sheets

OTHER PUBLICATIONS

Hendrickson, B.C., et al., "Identification of large genomic deletions in BRCA1 from patients with hereditary cancer risk using SNP haplotype pair analysis derived from clinical sequence data", *American Society of Human Genetics,* Oct. 2001; 1 page.

Brown, Melissa A., et al., "Germline BRCA1 Promoter Deletions in UK and Australian Familial Breast Cancer Patients: Identification of a Novel Deletion Consistent With BRCA1: Ψ BRCA1 Recombination", *Human Mutation,* 2002; 19:435–442.

Casilli, Federica, et al., "Rapid Detection of Novel BRCA1 Rearrangements in High–Risk Breast–Ovarian Cancer Families Using Multiplex PCR of Short Fluorescent Fragments", *Human Mutations,* 2002; 20:218–226.

Gad, Sophie, et al., "Significant contribution of large BRCA1 gene rearrangements in 120 French breast and ovarian cancer families", *Oncogene,* 2002; 21:6841–6847.

Hofmann, W., et al., "Detection of large rearrangements of exons 13 and 22 in the BRCA1 gene in German families", *J. Med. Genet.;* 2002; 39:1–2.

Ward, Benjamin D., et al., "Identification of a novel 26 kb deletion in BRCA1 by SNP haplotype pair analysis", *American Society of Human Genetics,* Oct. 2002; 1 page.

Hendrickson, B.C., et al., "Application of haplotype pair analysis for the identification of hemizygous loci", *J. Med. Genet.,* 2003; 40:1–2.

Hendrickson, B.C., et al., "Prevalence Results for Five Recurrent BRCA1 Rearrangement Mutations in 7570 Analyses", *American Society of Human Genetics,* Nov. 2003; 1 page.

* cited by examiner

METHOD OF IDENTIFYING GENOMIC REARRANGEMENTS

RELATED U.S. APPLICATION

This application claims priority to U.S. Provisional Application Ser. No. 60/328,873, filed on Oct. 12, 2001, the content of which is incorporated herein in its entirety.

FIELD OF THE INVENTION

The present invention generally relates to bioinformatics, and particularly to methods for identifying an increased likelihood of hemizygosity and thus large gnomic rearrangements.

BACKGROUND OF THE INVENTION

A large number of monogenic human diseases are associated with genetic polymorphic variations or mutations in the so-called susceptibility genes. See generally, Cooper et al. in *The Metabolic and Molecular Bases of Inherited Diseases,* 1:259–291 (1995), Scriver et al., eds., McGraw-Hill, New York. One of the best-known and practically significant disease genes is the breast cancer susceptibility gene 1 (BRCA1), a tumor suppressor gene identified based on its genetic linkage to familial breast cancers. Mutations of the BRCA1 gene in humans are associated with predisposition to breast and ovarian cancers. In fact, BRCA1 and BRCA2 mutations are responsible for the majority of familial breast cancers. Inherited mutations in the BRCA1 and BRCA2 genes are responsible for approximately 7–10% of all breast and ovarian cancers. Women with BRCA mutations have a lifetime risk of breast cancer between 56% and 87%, and a lifetime risk of ovarian cancer between 27% and 44%.

With a large number of deleterious mutations identified in various disease susceptibility genes, genetic testing on patients to determine the presence or absence of such deleterious mutations proves to be an effective approach in detecting predispositions to diseases associated with such deleterious mutations. Indeed, genetic testing continues to grow in importance. For example, genetic testing is now commonly accepted as the most accurate method for diagnosing hereditary breast cancer and ovarian risk.

As is generally known in the art, humans are diploid, i.e., human autosomal genes are present in the genome in two copies. A mutation in one copy of a gene can be relevant even if the other copy of the gene is unaffected. This phenomenon is particularly notable in autosomal dominant genes such as BRCA1. However, most genetic testing approaches rely on the analysis of genetic materials amplified from patient samples that include a mixture of both gene alleles. The amplification techniques employed are typically indiscriminative of the two gene alleles in a diploid subject. For example, the most commonly utilized PCR-based genetic tests entail PCR amplification of different portions of both alleles of a gene and detecting mutations in those amplified portions by, e.g., sequencing or SNP detection, which may identify polymorphisms but cannot assign the identified variants to specific alleles. A more serious limitation inherent in such approaches is that they are not suitable for detecting genomic rearrangements (e.g., deletions or duplications) especially when a large rearrangement occurs in one but not the other allele. Because the techniques do not differentiate different alleles, if one allele is wild type and the other allele has a large deletion, the analysis result based on the techniques would show wild-type. The result misrepresents homozygosity as hemizygosity.

Mutations in many disease susceptibility genes are dominant mutations, i.e., mutations in only one allele of a patient are often sufficient to predispose the patient to diseases even if the other allele is wild type. This is especially true with large genomic rearrangements. Therefore, it is important to identify all mutations including large genomic rearrangements. It will be particularly advantageous to complement traditional screening techniques that fail to distinguish between homozygous and hemizygous states with a method that can detect large genomic rearrangements.

SUMMARY OF THE INVENTION

The present invention provides a method that meets the need for identifying large genomic rearrangements based on unphased genotype data. The method is particularly applicable to genotyping techniques that do not differentiate different alleles. In the method, unphased genotypes at a plurality of nucleotide variant markers of a particular gene in a diploid subject are compared with a canonical haplotype collection of the gene from a representative heterogeneous subject population. Each of the canonical haplotypes comprises the plurality of nucleotide variant markers, as present on a single chromosome of each subject within the reference population. If the unphased genotypes cannot be reduced to a pair of canonical haplotypes within the canonical haplotype collection, it would indicate an increased likelihood that an allele of the gene in the diploid subject harbors a genomic large rearrangement.

The present invention also provides computer program products comprising a computer-usable medium having computer-readable program code or instructions embodied thereon for enabling a processor to carry out the method of the present invention. In addition, systems and Internet nodes for carrying out the methods of the present invention are also disclosed.

Thus, unphased genotypes obtained by any conventional genotyping methods can be analyzed by the method of the present invention. In addition, the method can be embodied in computer program products. As a result, large data can be quickly and accurately analyzed by a computer. The method can be used in genetic testing to identify large genomic rearrangements that are not detectable by traditional techniques, thus increasing the accuracy of predisposition prediction. In addition, the present invention has applications in many other areas of genetic research. For example, various SNP mapping projects and pharmacogenomic studies are generating large volumes of SNP data typically by approaches indiscriminative of the two gene alleles in diploid subjects. The method of the present invention can be applied to such SNP data to facilitate the detection of large genomic rearrangements in only one of the two alleles in a diploid subject, thus improving the data by identifying the not entirely confounding results. Therefore, the method can help to improve the accuracy of the SNP data and extract additional useful information from such SNP data.

The foregoing and other advantages and features of the invention, and the manner in which the same are accomplished, will become more readily apparent upon consideration of the following detailed description of the invention taken in conjunction with the accompanying drawings and examples, which illustrate preferred and exemplary embodiments.

DETAILED DESCRIPTION OF THE INVENTION

Figure 1:
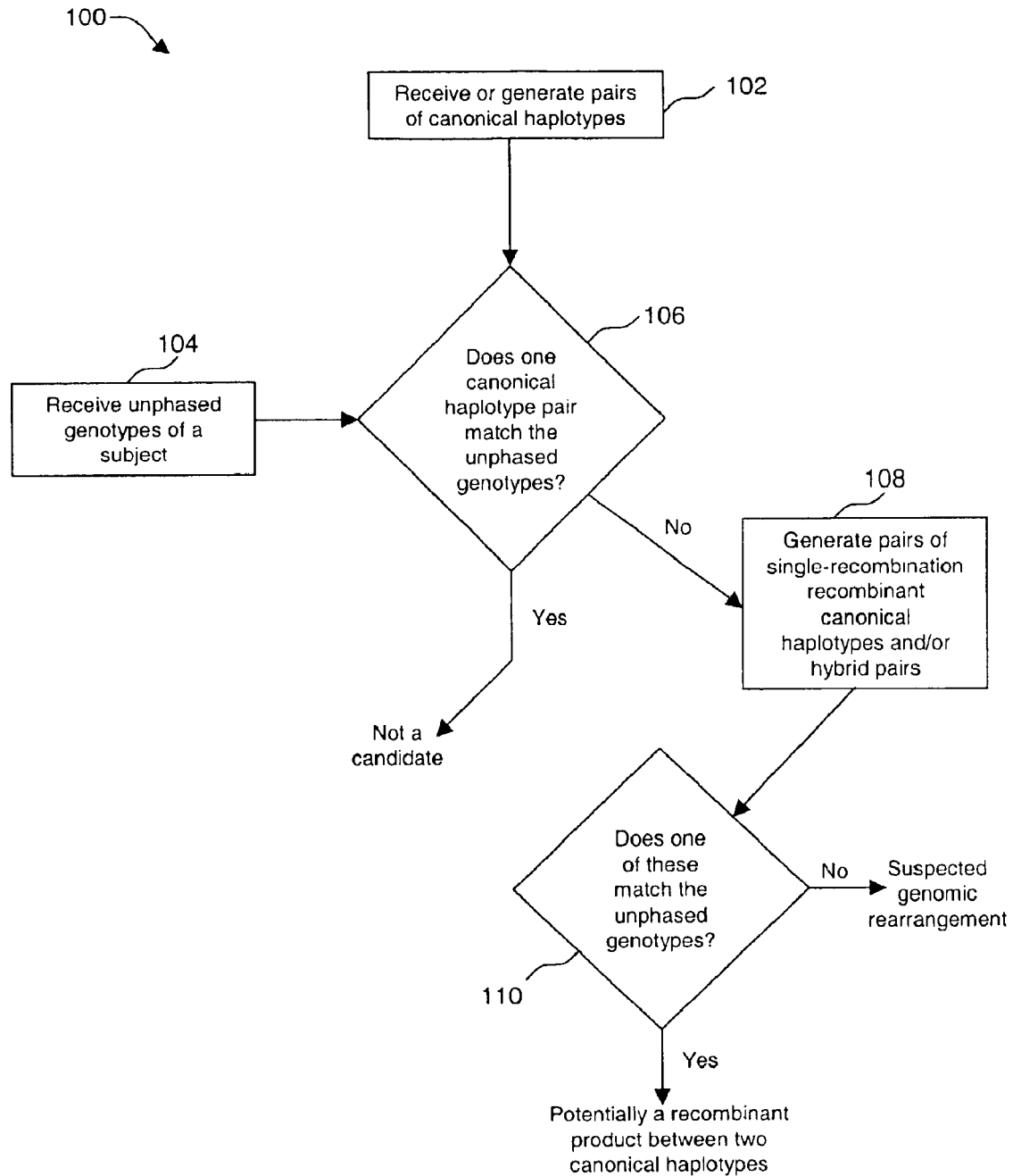
FIG. 1 is a flowchart illustrating an embodiment of the method and computer program product according to the present invention.

The present invention provides a method for detecting an increased likelihood of a genomic rearrangement in an allele of a gene (or a chromosomal region) of a diploid subject. In the method, unphased genotypes at a plurality of nucleotide variant markers from both alleles of a particular gene (or a particular chromosome region) in a diploid subject are compared with a canonical haplotype collection within the gene (or a particular chromosome region) in a heterogeneous subject population. Each of the canonical haplotypes comprises the plurality of nucleotide variant markers. If the unphased genotypes cannot be reduced to a pair of canonical haplotypes within the canonical haplotype collection, it would indicate an increased likelihood that an allele of the gene in the diploid subject harbors a genomic rearrangement.

As used herein, the term "diploid subject" means any diploid biological organisms including, but not limited to, fruit flies, mice, rats, sheep, cattle, monkeys, and human.

The term "allele" is used herein to refer generally to one copy of a naturally occurring gene or a particular chromosome region in a diploid subject. A diploid subject has two sets of chromosomes and two copies of a particular gene, and thus two haplotypes of any region of the chromosome and two alleles of any polymorphic site within the gene or chromosome region.

The term "nucleotide variant marker" means a nucleotide or nucleotide sequence at a particular locus of an allele of a gene (or a particular chromosome region), where two or more variants are found in a population. Examples of such variants include single nucleotide polymorphisms (SNPs) (including single nucleotide substitutions, insertions or deletions).

As used herein, the term "genomic rearrangement" means a physical change in a chromosome of a diploid subject that results in an increase or decrease of the copy number of one or more particular nucleotide variant markers within a particular haplotype of interest. Typically, the physical change is such that it may not be determinable in one or more traditional genotyping methods that employ amplification techniques indiscriminative of the two alleles in a diploid subject. Examples of such chromosomal physical changes include genomic deletions and duplications, preferably large genomic deletions or duplications of a contiguous of at least 10 base pairs, 100 base pairs, 500 base pairs, 1000 base pairs, 2000 base pairs, or 5000 base pairs or greater.

As used herein, the term "haplotype" means a combination of genetic (nucleotide) variants in a genomic DNA region on a single chromosome found in an individual or an mRNA derived from a single chromosome found in an individual. Thus, a haplotype includes a number of genetically linked "nucleotide variant markers" which are typically inherited together as a unit. The number of markers in a haplotype should be at least 3, preferably at least 4, and more preferably at least 5, most preferably at least 8, 9 or 10.

The term "canonical haplotypes" is used herein to generally refer to the haplotypes that commonly exist in a defined heterogeneous population of a subject species (a heterogeneous subject population). A "canonical haplotype collection" means a collection of canonical haplotypes representative of all canonical haplotypes in a defined heterogeneous subject population. Typically, a canonical haplotype collection consists of canonical haplotypes having a frequency in the defined population of 1.5% or higher, preferably 1% or higher, or 0.5% or higher, or at least 0.1%. As will be apparent to skilled artisans, in determining the desirable lower limit of a canonical haplotype frequency in a canonical haplotype collection, one should take into consideration many different factors including the diversity of a heterogeneous population, the size of the chromosomal region covered by the haplotype, and the number of nucleotide variant markers contained within a particular haplotype of interest. For example, the more diverse a population is, the smaller the lower haplotype frequency limit should be. Also, the more nucleotide variant markers are contained within a haplotype of interest, the smaller the lower haplotype frequency limit should be. For purposes of the method of the present invention, it is preferably that the lower limit is set such that almost all the common known haplotypes in a particular chromosomal DNA region are included while rare haplotypes in the region representing large genomic rearrangements are excluded.

The term "heterogeneous" is used herein in contrast to "familial" populations, which are composed of a plurality of individuals related to each other. That is, a heterogeneous population is a non-familial population and can include diverse individuals genetically unrelated to each other.

A defined heterogeneous population can be a population representative of all individuals of the same species or a population representative of a group of individuals of a species which have characteristics distinct from individuals in other groups of the same species. For example, a heterogeneous human population can be a population representative of all human races, or a population representative of only one race, or a population representative of individuals in a geographical area (e.g., a province/state or a nation).

The term "single-recombination recombinant canonical haplotypes" means recombinant haplotypes that can be generated by a single-recombination event between canonical haplotypes.

The term "subject haplotype" means a haplotype of an individual subject being studied.

"Haplotype pair collection" as used herein means a collection of all possible haplotype pairs derived from, and composed of, the canonical haplotypes in a canonical haplotype collection and/or all possible haplotype pairs derived from, and composed of, single-recombination recombinant canonical haplotypes derived from the canonical haplotypes in a canonical haplotype collection, and/or all possible haplotype pairs that are combinations of a canonical haplotype and a single-recombination recombinant canonical haplotype. The haplotype pairs can include a pair of the same haplotype or a pair of different haplotypes.

The term "genotype" as used herein means the nucleotide characters at a particular nucleotide variant marker in either one allele or both alleles of a gene (or a particular chromosome region). When the term "unphased genotypes" is used in connection with a biallelic gene (or a particular chromosome region), unphased genotypes for a particular marker can be expressed, e.g., in the form of X/Y, wherein X is the genotype in one allele while Y is the genotype in the other allele, with allelic specificity undefined. That is, it is undetermined which of the two alleles X is associated with, and Y is associated with. Unphased genotypes for a plurality of markers can be X/Y at a marker, A/B at another marker, C/D at yet another marker, and so on. Methods for determining "unphased genotypes" are generally known in the art. For example, to determine unphased genotypes at a nucleotide variant marker region, DNA samples from a diploid subject can be sequenced in that nucleotide variant marker region with sequencing primers that are not allele specific.

The method of the present invention typically requires that canonical haplotypes in a defined population be provided. Preferably, a canonical haplotype collection is provided. A canonical haplotype collection can be provided in various methods known in the art. For example, as it is usually practically infeasible to analyze every individual subject in a large subject population, a sample population representative of a defined subject population can be analyzed. For a large heterogeneous subject population, preferably a heterogeneous sample population is analyzed. The sample population should contain a large enough number of individual subjects. Preferably a great number of the individuals within the sample population are genetically unrelated. The size of the sample population may be dependent upon desirable frequencies of the canonical haplotypes to be included in a canonical haplotype collection. Specifically, if the lowest frequency of a canonical haplotype in the collection is desired to be low, then the size of the sample population needs to be greater. In addition, the heterogeneity of the population also affects sample size selection. Empirical or statistical analysis can be done to determine the appropriate size of a sample population under specific circumstances, which would be apparent to skilled artisans. Typically, each of the canonical haplotypes in a canonical haplotype collection should have a frequency of 1.5% or 2% or greater, 0.5% or 1% or greater, and preferably at least 0.1% or 0.2%. Therefore, the sample population may contain at least 40, 80, 100, 200, or 500 individual subjects: In addition, as will be apparent to skilled artisans, the number of individual subjects that must be included in a sample population to determine canonical haplotypes is also dependent upon the available genetic variants, their proximity, and the complexity of the haplotypes that exist for the region of interest. For example, it is easier to define haplotypes for BRCA1 than BRCA2 due to the reduced complexity in BRCA1.

A number of different methods can be employed in obtaining a canonical haplotype collection for a particular gene (or a particular chromosome region) from the sample population, as is generally known in the art. A traditional technique is to derive haplotypes by family analysis, i.e., studying the genotypes within the family members of a number of families. Also, experimental techniques may be employed to determine the haplotypes of the gene (or a particular chromosome region) in each individual subject of the sample population. One known technique is to separate a pair of chromosomes from each other and determine the genotypes at a plurality of nucleotide variant markers in the gene sequence of interest in each of the chromosomes. The genotypes at the markers in one chromosome will constitute one haplotype and the genotypes at the markers in the other chromosome will constitute another haplotype. Alternatively, an allele-specific PCR technique or a similar method can be used for allele-specific amplification of each allele of the gene of interest (or a particular chromosome region), and the allele-specific genotypes at nucleotide variant markers are determined.

In other methods, unphased genotype data may be obtained from each individual subject in the sample population by conventional genotyping methods, e.g., by sequencing diploid DNA. Various statistical analysis methods and algorithms known in the art may be employed to deduce canonical haplotypes in the sample population. For example, the Clark method known in the art can be employed for haplotyping. See Clark, *Mol. Biol. Evol.*, 7:111–122 (1990); Clark et al., *Am. J. Hum. Genet.*, 63:595–612 (1998). Various other haplotyping methods known in the art may also be used. See e.g., Maclean & Morton, *Genet. Epid.*, 2:263–272 (1985); Excoffier & Slatkin, *Mol. Biol. Evol.*, 12:921–927 (1995); Hawley & Kidd, *J. Hered.*, 86:409–411 (1995); Long et al., *Am. J. Hum. Genet.*, 56:799–810 (1995).

Preferably, single-recombination recombinant canonical haplotypes are also provided based on the canonical haplotypes. That is, a single recombination event can be imagined between two canonical haplotypes, the recombination occurring within a region between any two nucleotide variant markers of the canonical haplotypes. The two resulting haplotypes are single-recombination recombinant canonical haplotypes. Preferably, a collection of all single-recombination recombinant canonical haplotypes that can be generated from the canonical haplotypes in a canonical haplotype collection is deduced. Also preferably, a collection is provided including canonical haplotypes representative of a defined population as well as all possible single-recombination recombinant canonical haplotypes that can be generated from the canonical haplotypes.

Preferably, in accordance with the present invention, a haplotype pair collection is also provided based on the canonical haplotypes and/or single-recombination recombinant canonical haplotypes. The haplotype pair collection can include all possible haplotype pairs that can be derived from, and composed of, canonical haplotypes and single-recombination recombinant haplotypes. Alternatively, the haplotype pair collection can include only those haplotype pairs derived from, and composed of, canonical haplotypes. Or, the haplotype pair collection can include only those haplotype pairs derived from, and composed of, single-recombination recombinant haplotypes.

Thus, in one embodiment of the method of the present invention, unphased genotypes of the gene(s) of interest (or a particular chromosome region) in a particular diploid subject are determined at 3, preferably at least 4, 5, 6, 7 or at least 8 of the nucleotide variant markers of a canonical haplotype. Canonical haplotypes are provided from a population of the same species as the particular diploid subject. The unphased genotypes at a plurality of nucleotide variant markers are compared with the canonical haplotypes to determine if the unphased genotypes at the nucleotide variant markers can be reduced to a pair of the canonical haplotypes. Preferably, a canonical haplotype collection is provided using any techniques known in the art. Each of the canonical haplotypes in the canonical haplotype collection includes at least 3, preferably at least 4, 5, 6, 7 or at least 8 nucleotide variant markers within the gene of interest (or within a particular chromosome region). The canonical haplotype collection represents representative canonical haplotypes of a defined heterogeneous subject population. The unphased genotypes can be compared with the canonical haplotypes in the collection to determine if the unphased genotypes can be reduced to a pair of canonical haplotypes.

The pair can be homozygous (i.e., two same haplotypes form a pair) or heterozygous (i.e., two different haplotypes form a pair). If the answer is no, that is, the unphased genotypes cannot be reduced to a canonical haplotype pair, a conclusion can be reasonably made that there is an increased likelihood that an allele of the gene harbors a genomic rearrangement.

In another embodiment, a haplotype pair collection is provided from a canonical haplotype collection. Preferably, each of the canonical haplotypes in the haplotype pair collection includes at least 3, preferably at least 4, 5, 6, 7 or at least 8 nucleotide variant markers within a gene (or a particular chromosome region) of interest. The haplotype pair collection represents all possible haplotype pairs, whether homozygous or heterozygous, that can be derived from and composed of the canonical haplotypes in a canonical haplotype collection. In addition, unphased genotypes at 3, preferably at least 4, 5, 6, 7 or at least 8 of the nucleotide variant markers of a canonical haplotype are determined for the gene (or a particular chromosome region) of interest in a particular diploid subject. Such unphased genotypes are compared with the haplotypes pairs in the haplotype pair collection to determine if the unphased genotypes at the nucleotide variant markers can be reduced to a pair of canonical haplotypes. If the unphased genotypes at the plurality of nucleotide variant markers cannot be reduced to a canonical haplotype pair, a conclusion can be reasonably made that there is an increased likelihood that an allele of the gene harbors a genomic rearrangement.

Unphased genotypes that do not conform to canonical haplotypes can usually be explained in the following ways: (1) the subject tested contains a common haplotype from a population not previously encountered; (2) the tested subject contains a rare haplotype that is the product of recombination between canonical haplotypes or is a product of a point mutation(s); or (3) the tested subject is hemizygous due to a partial gene/chromosome deletion. Typically, when canonical haplotypes are derived from a well-selected representative heterogeneous population, the possibility of the first explanation is relatively low. To determine if the second explanation is appropriate, the unphased genotypes can be compared to any known haplotypes that are products of point mutations or any other known non-canonical haplotypes.

In a preferred embodiment of the method of the present invention, the unphased genotypes of a tested subject are also compared to single-recombination recombinant canonical haplotypes, in addition to canonical haplotypes. By comparing unphased genotypes of a specific subject being tested to canonical haplotypes as well as single-recombination recombinant canonical haplotypes, the power of prediction of an increased likelihood of genomic rearrangement is greatly increased.

For this purpose, for example, the unphased genotypes are compared to the haplotypes in a collection that includes canonical haplotypes representative of a defined population as well as all possible single-recombination recombinant canonical haplotypes that can be generated from the canonical haplotypes. The comparison step(s) will determine if the unphased genotypes can be reduced to two haplotypes (same or different) selected from the canonical haplotypes and the single-recombination recombinant canonical haplotypes.

Preferably, in specific embodiments, the method includes a step of providing a haplotype pair collection that includes all possible haplotype pairs derived from, and composed of, the canonical haplotypes in a canonical haplotype collection. In other specific embodiments, the method includes a step of providing a haplotype pair collection that includes, in addition to all possible canonical haplotype pairs, all possible single-recombination recombinant haplotype pairs derived from and composed of the single-recombination recombinant canonical haplotypes derived from the canonical haplotypes in a canonical haplotype collection. The haplotype pair collection may also include all haplotype pairs that are composed of a canonical haplotype and a single-recombination recombinant haplotype. When such an all inclusive haplotype pair collection is used in comparisons between the unphased genotypes of a gene (or a particular chromosome region) of a tested diploid subject and the canonical haplotypes and single-recombination recombinant canonical haplotypes for the gene (or the particular chromosome region) in a heterogeneous subject population, the detection power is greatly increased.

Particularly, in the case where all or most nucleotide variant markers of a haplotype are within the gene of interest, the frequency of double recombination within a single gene is typically low. If the unphased genotypes cannot constitute a pair of haplotypes selected from the group consisting of canonical haplotypes and single-recombination recombinant canonical haplotypes, then it is less likely that the tested subject contains a rare haplotype that is the product of recombination between canonical haplotypes. Rather, it is more likely that the tested subject harbors a genomic rearrangement in one of the two alleles.

In one embodiment, during the comparison between the unphased genotypes determined from the tested subject and the canonical haplotypes and/or single-recombination recombinant canonical haplotypes, the most likely subject haplotype pair, that is, the haplotype pair in the subject being tested, can be predicted based on the unphased genotypes and canonical haplotypes and/or single-recombination recombinant canonical haplotypes. Typically, the subject haplotype pair should be a pair that most resembles a pair of canonical haplotypes or a pair of single-recombination recombinant canonical haplotypes, or a combination of a canonical haplotype and a single-recombination recombinant canonical haplotype, among all possible haplotype pairs that can be deduced from the unphased genotypes.

In particular, if the predicted subject haplotype pair includes one subject haplotype identical to a first canonical haplotype and the other subject haplotype differs from all of the canonical haplotypes and preferably, also differs from all single-recombination recombinant canonical haplotypes, one can reasonably conclude that there is an increased likelihood that an allele of the gene (or a chromosome region) in the tested diploid subject harbors a genomic rearrangement. Further, if (1) the predicted subject haplotype pair includes the first subject haplotype identical to a first canonical haplotype, (2) the second subject haplotype differs from all of the canonical haplotypes and preferably, also from all single-recombination recombinant canonical haplotypes; (3) but for the genotypes at one or more adjacent nucleotide variant markers, the second subject haplotype would have been identical to a canonical haplotype distinct from the first subject haplotype; and (4) the unphased genotype(s) indicate homozygosity at the "one or more adjacent nucleotide variant markers," then it can be reasonably concluded that it is likely that the gene (or chromosome region) of interest is hemizygous at the "one or more adjacent nucleotide variant markers," and it is likely that the gene (or chromosome region) harbors a deletion at those one or more adjacent nucleotide variant markers in one allele but not the other allele.

Once it is determined that there is an increased likelihood that an allele of a gene of interest in the tested diploid subject harbors a genomic rearrangement, several approaches can be employed for further analysis. Most importantly, an understanding of the events required to convert a canonical haplotype into the unusual haplotype found in the test subject would be helpful. Genetic events that lead to changes in haplotypes include point mutations and recombination. The simpler the path of events that could result in conversion of a canonical haplotype to the potential unusual haplotype, the less likely it is for the unusual haplotype to represent a genomic rearrangement. For example, a deduced subject haplotype that could be explained as a single recombination event or single point mutation event in or between canonical haplotypes is less likely to represent a deletion than a haplotype that would require multiple events to achieve the same explanation. The proximity of the nucleotide variant markers involved in the events required to convert a canonical haplotype to a deduced subject haplotype can also impact the assessment of the probability that a haplotype represents a deletion. For example, genetic recombination is less likely to occur between loci with close proximity. The sequence context of the loci involved in the events also impacts this assessment. The scientific literature supports the assertion that most deletions involve homologous recombination between repetitive elements within a genome. In humans, Alu elements are probably most important sequences that can lead to recombination. Therefore, the potential for a genotype to represent a deletion is impacted by the ability to explain this circumstance by homologous recombination.

Another factor to be considered is that the deduced unusual subject haplotype may be explained as a haplotype not previously encountered and may not represent the existence of a genomic rearrangement. However, generally, as discussed above, if the canonical haplotypes are provided based on a well representative heterologous population, the likelihood of such newly encountered haplotypes is low. As a precaution, ancestries of the test subject may be examined for their genotypes and haplotypes to determine if indeed the unusual haplotype is a new population-specific haplotype and does not represent a deletion event.

As is clear from the disclosure herein, albeit such further analysis, the comparison steps of the method of the present invention can substantially enrich the very rare samples containing genomic rearrangements.

The analysis by the method of the present invention can lead to the generation of information or data indicating the presence or absence of a genomic rearrangement in a particular gene or chromosome region and the approximate location thereof. For example, the data may include information relating to the identity of the individuals tested, the identity of the genes (or chromosome regions) analyzed, the likelihood of a genomic rearrangement, and the location of the detected genomic arrangement (e.g., expressed relatively to nucleotide variant markers), etc. Alternatively, the data set may simply include assigned identification numbers understood by the researchers conducting the screening assay and/or researchers receiving the data set as representing specific analysis results. The data or information can be cast in a transmittable form (i.e., transmittable data product) that can be communicated or transmitted to other researchers, particularly researchers in a different country. Such a transmittable form can vary and can be tangible or intangible. For example, the data defining a test result can be embodied in texts, tables, diagrams, molecular structures, photographs, charts, images or any other visual forms. The data or information can be recorded on a tangible media such as paper or embodied in computer-readable forms (e.g., electronic, electromagnetic, optical or other signals). The data in a computer-readable form can be stored in a computer usable storage medium (e.g., floppy disks, magnetic tapes, optical disks, and the like) or transmitted directly through a communication infrastructure. In particular, the data embodied in electronic signals can be transmitted in the form of email or posted on a website on the Internet or Intranet. In addition, the information or data can also be recorded in an audio form and transmitted through any suitable media, e.g., analog or digital cable lines, fiber optic cables, etc., via telephone, facsimile, wireless mobile phone, Internet phone and the like.

Thus, the information or data can be produced anywhere in the world and transmitted to a different location. For example, when an analysis by the method of the present invention is conducted offshore, the information or data generated can be cast in a transmittable form as described above. The data and information in a transmittable form thus can be imported into the U.S. or transmitted to any other countries, where the data and information may be used in further testing, analysis, or experimental/industrial use.

Once a potential genomic rearrangement is detected, laboratory bench analysis can be performed to confirm the presence of the genomic rearrangement, and further characterize the genomic rearrangement, as illustrated in the example below.

The method of the present invention can be implemented using hardware, software or a combination thereof in one or more computer systems or other processing systems. The method of the present invention can be implemented in any suitable language and/or browsers.

For example, the method may be implemented with C language and preferably using object-oriented high-level programming languages such as SmallTalk, C++, and the like. The application can be written to suit environments such as the Microsoft Windows™ including Windows™ 98, Windows™ 2000, Windows™ NT, and the like. In addition, the application can also be written for the MacIntosh™, SUN™, UNIX or LINUX environment. In another example, the method can be implemented using a universal or platform-independent programming language. Examples of such multi-platform programming languages include, but are not limited to, hypertext markup language (HTML), JAVA™, JavaScript™, Flash programming language, common gateway interface/structured query language (CGI/SQL), practical extraction report language (PERL), programming language/structured query language (PL/SQL), and the like. Java™—or JavaScript™—enabled browsers such as HotJava™, Netscape™, and Microsoft™ Explorer™ can be used. When active content web pages are used, they may include Java™ applets or ActiveX™ controls or other active content technologies.

Thus, the method of the present invention can be embodied in computer program products and used in computer- or internet-based systems. Accordingly, another aspect of the present invention relates to a computer program product comprising a computer-usable medium having computer-readable program code or instructions embodied thereon for enabling a processor to carry out the method of the present invention. Typically, the computer-readable program code in the computer program product of the invention enables a computing system to compare the unphased genotypes with canonical haplotypes, preferably with canonical haplotype pairs within a haplotype pair collection. More preferably, the unphased genotypes are also compared with single-recombination recombinant canonical haplotypes, or single-recombination recombinant canonical haplotype pairs and/or haplotype pairs composed of a canonical haplotype and a single-recombination recombinant canonical haplotype.

Preferably, the computer-readable program code enables a computer system to receive information representative of unphased genotypes at a plurality of nucleotide variant markers in a gene (or a particular chromosome region) of interest of a diploid subject. In addition, preferably the computer-readable program code in the computer program product also enables the computer system to receive or generate information or data representative of canonical haplotypes or canonical haplotype collections.

In one embodiment, the computer-readable program code enables the computer system incorporating or running the computer program product or the computer-readable program code therein to receive or generate information on canonical haplotypes pairs and receive information on unphased genotypes of a tested subject. The computer-readable program code then enables comparison between the unphased genotypes and the canonical haplotype pairs to determine if a canonical haplotype pair matches the unphased genotypes, i.e., if the unphased genotypes can be reduced to a canonical haplotype pair. If the answer is yes, the computer system stops the analysis. If the answer is no, then optionally the computer-readable program code enables the computer system to generate or receive single-recombination recombinant canonical haplotype pairs and compare the unphased genotypes with the single-recombination recombinant canonical haplotype pairs. The single-recombination recombinant canonical haplotype pairs can also be generated in an earlier step. If the computer system finds a single-recombination recombinant canonical haplotype pair that matches the unphased genotypes, it stops there. If the answer is no, then the computer system will conclude and indicate the result—there is an increased likelihood that the tested subject is hemizygous and harbors a genomic rearrangement in one allele of the gene of interest. Preferably, the computer-readable program code is also capable of enabling the computer system to receive or generate data or information representative of haplotype pairs composed of a canonical haplotype and a single-recombination recombinant canonical haplotype and to compare that with the unphased genotypes. It is noted that the receipt/generation of the different types of haplotypes/haplotype pairs and/or comparison thereof with unphased genotypes can be conducted in simultaneously in the same steps, or separately in different steps.

FIG. 1 is a flowchart illustration of an embodiment of the methods and program products according to the invention. The process 100 is preferably carried out by a processor (e.g., a computer) under the instructions of a computer-readable program code. Essentially, process 100 includes a step 102, in which canonical haplotype pair collection is received or generated representative of canonical haplotype pairs found in a defined subject population. In addition, information or data on unphased genotypes of a diploid subject being studied at a plurality of nucleotide variant markers are provided or received in step 104. In the comparison step (step 106), the unphased genotype of the test diploid subject at each of the plurality of nucleotide variant markers is analyzed and compared to each canonical haplotype pair received or generated in step 102, to determine if the unphased genotypes match one of the canonical haplotype pairs. If the answer is yes, then the processor stops the analysis on that diploid subject and provides a signal that no genomic arrangement is detected for that diploid subject.

If the result in step 106 is negative, the system performs step 108 to generate or receive a collection of pairs of single-recombination recombinant canonical haplotypes and pairs including a canonical haplotype and a single-recombination recombinant canonical haplotype. In step 110, it is determined whether one of the pairs in the collection received or generated in step 108 matches the unphased genotypes of the diploid subject being studied. If the answer is yes, the processor would indicate that the diploid subject contains a recombinant product between two canonical haplotypes. If the result in step 110 is negative, that is, the unphased genotypes of the diploid subject of interest cannot be reduced to a haplotype pair selected from the collection in step 108, then the process should provides an indication that there is an increased likelihood that the diploid subject harbors a genomic rearrangement.

As will be apparent to skilled artisans, process 100 can be modified in a variety of ways and yet the same results can still achieved. For example, steps 102 and 108 can be combined into one step, and as a result, steps 106 and 110 can also be combined into a single step.

Figure 2:
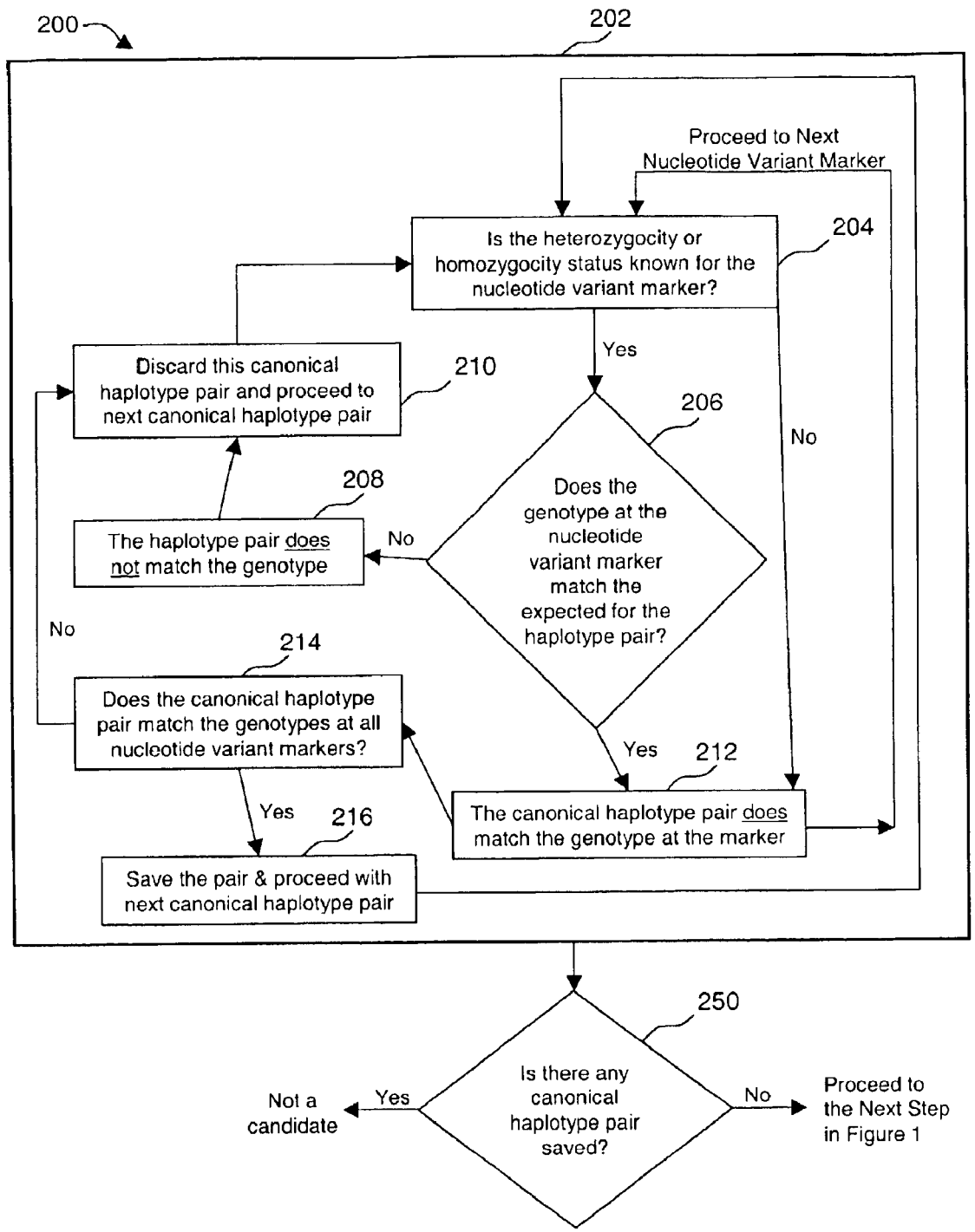
FIG. 2 is a flowchart illustrating an example of the comparison step in the flowchart of FIG. 1.

FIG. 2 is another flowchart illustrating an exemplary procedure 200 for the comparison step 106 in the process 100 shown in FIG. 1. First, as shown in the flowchart of FIG. 2, whether the heterozygocity or homozygosity status is known for the unphased genotypes of the test diploid subject at the first nucleotide variant marker is determined in step 204. If the status is unknown, it is presumed that the unphased genotypes match the genotypes at the corresponding nucleotide variant marker of a canonical haplotype pair (step 212), and the unphased genotypes at the first nucleotide valiant marker are skipped and the unphased genotypes of the test diploid subject at the second nucleotide variant marker are analyzed.

However, if the status at the first marker is known, the unphased genotypes at that nucleotide variant marker are compared with a first canonical haplotype pair to determine if the unphased genotypes match the genotypes of that canonical haplotype pair at the corresponding nucleotide variant marker (step 206). If there is a match, that same haplotype pair is compared to the unphased genotypes at the second nucleotide variant marker in the same manner described above. That is, whether the heterozygocity or homozygosity status is known for the unphased genotypes at the second nucleotide variant marker is determined (step 204). If the status is known, the unphased genotypes at the second nucleotide variant marker are compared to the first canonical haplotype pair to determine if the unphased genotypes match the genotypes of that canonical haplotype pair at the corresponding nucleotide variant marker (step 206). Thus, the unphased genotypes at each of the plurality of nucleotide variant markers are analyzed sequentially until a non-match result is generated, that is, until the unphased genotypes at a nucleotide variant marker of the test subject are found not matching the genotypes at the corresponding nucleotide variant marker in this first canonical haplotype pair. In that event, the canonical haplotype pair is discarded and will not be used in subsequent analyses (steps 208 and 210).

If a non-match result is not generated using the first canonical haplotype pair after analyzing the unphased genotypes at all of the plurality of nucleotide variant markers, that canonical haplotype pair is saved rather than discarded (steps 214 and 216). Then a second canonical haplotype pair is used in the same manner in another round of analysis against the unphased genotypes at each of the plurality of nucleotide variant markers. Typically, once a canonical haplotype pair is saved, the analysis can be stopped there (step 250). Alternatively, the analysis can proceed until every canonical haplotype pair is analyzed against the unphased genotypes of the test subject at all of the nucleotide variant markers. In the end, it will be determined whether or not there is a canonical haplotype pair saved (step 250). If the answer is yes, then an increased likelihood of genomic rearrangement is not detected and the test diploid subject is not considered a candidate for further analysis, as is shown in both FIG. 2 and FIG. 1. however, if there no canonical haplotype pair saved, then it can be concluded that there is an increased likelihood that a genomic rearrangement is harbored in one of the two alleles in the tested diploid subject.

Optionally, a comparison analysis is performed in the same manner with single-recombinant canonical haplotype pairs and/or haplotype pairs that include a canonical haplotype and a single-recombination recombinant canonical haplotype (see step 108 in FIG. 1). Of course, the single-recombinant canonical haplotype pairs can also be combined with canonical haplotype pairs and optionally hybrid haplotype pairs (i.e., each pair includes a canonical haplotype and a single-recombinant canonical haplotype) in a haplotype pair collection and are used in the same comparison analysis steps 202 and 205 as described above.

It will be understood that each block or step of the flowchart illustrations and combinations of blocks in the flowcharts can be implemented by computer program instructions. These computer program instructions may be loaded onto a computer or other programmable apparatus to produce a machine, such that the instructions which execute on the computer or other programmable apparatus create means for implementing the functions specified in the flowcharts or step(s). These computer program instructions may also be stored in a computer-readable memory or medium that can direct a computer or other programmable apparatus to function in a particular manner, such that the instructions stored in the computer-readable memory or medium produce an article of manufacture including instruction means which implement the function specified in the flowcharts or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the flowcharts or step(s).

Accordingly, the flowcharts support combinations of means for performing the specified functions, combinations of steps for performing the specified functions and program instruction means for performing the specified functions. It will also be understood that each step of the flowcharts and combinations of steps in flowcharts can be implemented by special purpose hardware-based computer systems which perform the specified functions or steps, or combinations of special purpose hardware and computer instructions.

Thus, the present invention further provides a system for detecting an increased likelihood of a genomic rearrangement in an allele of a gene of a diploid subject. The system typically is driven by computer-readable program code of the present invention. Generally, the system includes an interface module for receiving information representative of unphased genotypes at a plurality of nucleotide variant markers in a biallelic gene (or chromosome region) of interest in a diploid subject being studied. The interface module can be designed and structured such that it can receive direct manual input of data by a user. Alternatively, the interface module can be in a form that can access a database including information on the unphased genotypes of the diploid subject being studied. The interface module can also be designed to retrieve information directly from a system used for genotyping (e.g., a automatic sequencer, a microarray reader, etc.)

In addition, the system can also include an interface module for receiving information representative of a haplotype collection including canonical haplotypes and/or single-recombination recombinant canonical haplotypes, and/or a haplotype pair collection including pairs of canonical haplotypes and/or single-recombination recombinant canonical haplotypes for a gene (or chromosome region) of interest in a heterogeneous subject population. The information can be manually input by a user. Alternatively, the interface module is made such that it can interface with a database containing information representative of a canonical haplotype collection and/or a canonical haplotype pair collection including canonical haplotypes and/or single-recombination recombinant canonical haplotypes for the gene (or chromosome region) of interest in a heterogeneous subject population.

The system can include a processor connected to the interface modules or database or physically separated from, but operably (e.g., electrically) connected to the interface modules or database. In either instance, it must be understood that the processor may consist of any number of devices. The processor may be a data processing device, such as a microprocessor or microcontroller or a central processing unit. The processor can be another type of logic device such as a DMA (Direct Memory Access) processor, an integrated communication processor device, a custom VLSI (Very Large Scale Integration) device or an ASIC (Application Specific Integrated Circuit) device. In addition, the processor can be any other types of analog or digital circuitry that are designed to perform the processing functions described herein.

Optionally, the system has a computer instructions means for enabling the processor to generate a canonical haplotype collection from unphased genotype data representative of a defined subject population. Also optionally, the system has a computer instructions means for enabling the processor to deduce all possible single-recombination recombinant canonical haplotypes from a canonical haplotype collection representative of a defined subject population.

In addition, the system can also have a computer instructions means for enabling the processor to generate a canonical haplotype pair collection from information representative of a canonical haplotype collection. Also, the system may also contain a computer instruction means to enable the processor to generate a collection of single-recombination recombinant canonical haplotypes pairs and/or hybrid haplotype pairs that include a single-recombination recombinant canonical haplotype and a canonical haplotype.

The system should contain a computer instructions means to cause the processor to compare the unphased genotypes with a haplotype pair collection which includes canonical haplotype pairs, and/or single-recombination recombinant canonical haplotype pairs, and/or hybrid haplotype pairs that include a single-recombination recombinant canonical haplotype and a canonical haplotype.

The system should display the comparison results through one of the two interface modules described above or a third interface module or a display device integrated with the processor, or alternatively, physically separated but operably (e.g., electrically) connected to the processor. For example, if the unphased genotypes do not match any of the canonical haplotype pairs and/or single-recombination recombinant canonical haplotype pairs and/or the hybrid haplotype pairs, the system will display a positive result indicating an increased likelihood that an allele of the gene (or chromosome region) in the diploid subject harbors a genomic rearrangement. Otherwise, the system will display a negative result.

It should also be understood that the system of the present invention is intended to encompass various embodiments of internet applications of the present invention, e.g., an internet node or intranet node. Such a node should include an interface module for receiving or accessing information representative of unphased genotypes and an interface module for receiving information representative of a canonical haplotype collection and/or a haplotype pair collection including canonical haplotypes and/or single-recombination recombinant canonical haplotypes for the gene (or chromosome region) of interest in a heterogeneous subject population. Optionally, a single interface module may be used to perform the above interfacing functions. The node may also include a computer instructions means for generating a canonical haplotype pair collection from information representative of a canonical haplotype collection, and optionally a collection of single-recombination recombinant canonical haplotypes and/or a collection of single-recombination recombinant canonical haplotype pairs and/or hybrid haplotype pairs.

Thus, the present invention provides a method for predicting based on unphased genotypes whether or not a diploid test subject is likely to be hemizygous for a particular biallelic gene (or chromosome region) and thus harbor a genomic rearrangement in one of the two alleles. The invention can enrich very rare samples containing deletions to a great proportion. Furthermore, the method can utilize any existing data and the computations can be fully automated. Samples highly enriched to contain large genomic rearrangements make analysis to find these mutations feasible and cost effective. Once the genomic rearrangements are characterized, this information permits the development of inexpensive and sensitive genetic tests that can be employed clinically. In addition, the method of the present invention can also be applied to large volumes of SNP data generated in various SNP mapping projects to facilitate the detection of large genomic rearrangements in only one of two alleles, thus improving the accuracy of the SNP data and extracting additional useful information from such SNP data.

EXAMPLE

DNA sequencing is employed in clinical genetic testing where circumstances warrant whole gene heteroduplex analyses with the highest levels of sensitivity. A by-product of this method includes detailed single nucleotide polymorphism (SNP) information. These data have applications in determining SNP haplotypes using Hardy-Weinberg principles outside of information about family structures.

Clinical testing for predisposition to breast/ovarian cancer in approximately 15,000 patients by full gene DNA sequencing (BRACAnalysis) has produced extensive information about genetic variation in BRCA1 and BRCA2. Ten clearly defined SNP haplotypes based on 14 polymorphisms located within and near the exons of BRCA1 were identified by applying Expectation-Maximization analysis to this data set.

Genotypes that do not conform to these haplotype definitions can usually be explained in the following ways: The sample contains a common haplotype from a population not previously encountered. The sample contains a rare haplotype that is the product of recombination between known haplotypes or the product of a point mutation(s). The sample presents an apparent haplotype that results from hemizygous loci due to a partial gene deletion. The low complexity of BRCA1 haplotypes facilitates the selection of samples where the latter case is most likely.

In this study, patients were identified as candidates to evaluate for large genomic deletions due to family history of breast and/or ovarian cancer combined with a negative clinical test result for mutations within BRCA1 and BRCA2. SNP haplotype pair analysis was performed on approximately 1000 samples meeting this criteria using DNA sequence data obtained during clinical testing. The method illustrated in the flowcharts in FIGS. 1 and 2 was used in this analysis. A group of fourteen samples were identified that possessed rare haplotypes suggestive of large genetic rearrangements involving BRCA1 exon 16. These fourteen samples were rare variants on a common haplotype (common type 2 haplotype) made up of eight polymorphisms that exist between exons 9 and 16. Type 2 haplotype is defined with the following polymorphisms: IVS8-58delT, S694S (C>T cDNA 2201), L771L (T>C cDNA 2430), P871L (C>T cDNA 2731), E1038G (A>G cDNA 3232), K1183R (A>G cDNA 3667), S1436S (T>C cDNA 4427), S1613G (A>G cDNA 4956). The samples in this set of fourteen were heterozygous for these eight polymorphisms except that the SNP responsible for S1613G (exon 16) was homozygous or potentially hemizygous (8 GGT and 6 AGT). The fourteen samples in this set represented various ethnic groups. Two samples indicated that their ancestry was African American, four indicated Eastern or Western European, four indicated Caribbean/Latin American ancestry, and the remaining four did not specify their ancestry or it was unknown.

To verify the existence of large genomic rearrangements in such samples, long range PCR was performed on the fourteen samples with the candidate haplotypes. Primers were used that amplified a 12.9 kb region from exon 14 through exon 18. Visualization of the amplified product on an agarose gel stained with ethidium bromide revealed seven samples that produced mutant fragments suggestive of large deletions. These results indicated that a variety of deletions have occurred in this region of the gene. Restriction digests of the gel purified mutant fragments with the enzymes HincII or PvuII showed that all seven samples contain deletions of multiple exons. The restriction map of the mutant fragment generated from one of the seven samples suggested a deletion of exons 15 and 16. The remaining six samples contained deletions of exons 16 and 17.

The deletion breakpoints were characterized by fluorescent nucleotide sequencing. A matrix of primers was designed around each of the suspected breakpoint regions identified by restriction digest analysis. Primer combinations were tested until a mutant fragment was generated that was small enough to sequence. Analysis of the sequence traces revealed five unique deletions in the seven samples:

Deletion #1 was identified in three patients that claimed Caribbean/Latin American ancestry. The rearrangement removes 6,337 bases that include exons 16 and 17.

Deletion #2 was identified in one sample with European ancestry. The deletion comprises 7,184 bases and removes exons 16 and 17.

Deletion #3 was identified in one sample of unknown ancestry, removes exons 16 and 17, and is 6,157 bases in size.

Deletion #4 was characterized in a sample of African American ancestry. The deletion is 5,761 bases in size and also removes exons 16 and 17.

Deletion #5 was identified in a sample with European ancestry. The rearrangement removes 5,629 bases that include exons 15 and 16.

The deletions of exons 16 and 17 (deletions #1–4) would change the protein structure by removing 133 amino acid residues (E1559–T1690). Although the open reading frame is preserved, 42 residues of the 5' BRCT domain (amino acids 1649–1736) are deleted. When exons 15 and 16 are deleted (deletion #5) the open reading frame is preserved through residue R1495, followed by thirteen abnormal residues and an ochre stop codon.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for detecting an increased likelihood of a genomic rearrangement in an allele of a diploid subject, said method comprising the steps of:

providing a haplotype collection comprising canonical haplotypes and single-recombination recombinant canonical haplotypes for a chromosome region in a heterogeneous subject population, each of said canonical haplotypes and single-recombination recombinant canonical haplotypes comprising a plurality of nucleotide variant markers;

providing unphased genotypes at said plurality of nucleotide variant markers in said chromosome region in said diploid subject; and comparing said unphased genotypes with said canonical haplotypes and said single-recombination recombinant canonical haplotypes, wherein a result that said unphased genotypes cannot be reduced to a pair of haplotypes formed by said canonical haplotypes and/or said single-recombination recombinant canonical haplotypes would indicate an increased likelihood that an allele of said chromosome region in said diploid subject harbors a genomic rearrangement.

2. The method of claim 1, wherein said diploid subject is a mammal.

3. The method of claim 1, wherein said diploid subject is a human.

4. The method of claim 1, wherein the unphased genotypes suggest a heterologous haplotype pair including one haplotype identical to a first canonical haplotype or single-recombination recombinant canonical haplotype, while the other haplotype is different from all of the canonical haplotypes and single-recombination recombinant canonical haplotypes, and differs from one of the canonical haplotypes by one or more adjacent nucleotide variant markers.

5. The method of claim 1, wherein each of said canonical haplotypes are present in said heterogeneous subject population at a frequency of at least 1%.

6. The method of claim 1, wherein each of said canonical haplotypes includes at least 8 nucleotide variant markers.

7. The method of claim 1, wherein said step of providing the unphased genotypes at each of said plurality of nucleotide variant markers comprises indiscriminative PCR amplification of both alleles of said chromosome region and DNA sequencing the amplified products.

8. The method of claim 1, further comprising isolating the chromosome region of said allele that is detected to have an increased likelihood of harboring a genomic rearrangement, and sequencing the region.

9. The method of claim 1, further comprising providing a haplotype pair collection including pairs of haplotypes selected from the group consisting of said canonical haplotypes and said single-recombination recombinant canonical haplotypes, wherein the unphased genotypes are compared with said pairs of haplotypes to determine whether one of said haplotype pairs matches the unphased genotypes.

10. The method of claim 1, wherein said plurality of nucleotide variant markers are located within one gene.

11. A method for identifying a gene allele harboring a genomic deletion in a diploid subject, said method comprising the steps of:

providing canonical haplotypes for said gene in a heterogeneous subject population, each of said canonical haplotypes comprising at least 5 nucleotide variant markers within said gene;

providing single-recombination recombinant canonical haplotypes based on said canonical haplotypes;

generating a haplotype pair collection comprising pairs of haplotypes selected from the group consisting of said canonical haplotypes and said single-recombination recombinant canonical haplotypes;

providing unphased genotypes at said at least 5 nucleotide variant markers in said gene of said diploid subject, wherein said unphased genotypes are determined by indiscriminative PCR amplification of both alleles of a portion of said gene and sequencing the amplified products; and comparing said unphased genotypes with said pairs of haplotypes, wherein an increased likelihood that the gene harbors a genomic deletion is predicted if the unphased genotypes can be reduced to a heterologous haplotype pair including (1) one haplotype identical to a canonical haplotype or single-recombination recombinant canonical haplotype, and (2) the other haplotype different from all of the canonical haplotypes and single-recombination recombinant canonical haplotypes, and different from one of the canonical haplotypes by one or more adjacent nucleotide variant markers.

12. The method of claim 11, further comprising isolating a portion of the gene of said allele that is predicted to have an increased likelihood of harboring a genomic rearrangement, and sequencing the portion.

13. A method for detecting an increased likelihood of a genomic rearrangement in an allele of a chromosome region of a diploid subject, said method comprising:

comparing unphased genotypes at a plurality of nucleotide variant markers in both alleles of said chromosome region in said diploid subject with canonical haplotypes for said chromosome region in a heterogeneous subject population, each of said canonical haplotypes comprising said plurality of nucleotide variant markers; and predicting, from said unphased genotypes, a pair of subject haplotypes that most resemble one or two members of said canonical haplotypes, wherein a result that the subject haplotype pair includes one haplotype identical to a first canonical haplotype and the other haplotype differs from all of the canonical haplotypes would indicate an increased likelihood that an allele of said gene in said diploid subject harbors a genomic rearrangement.

14. The method of claim 13, further comprising comparing said unphased genotypes with single-recombination recombinant canonical haplotypes, wherein the fact that the subject haplotype pair includes one haplotype identical to a first canonical haplotype or single-recombination recombinant canonical haplotype, and the other haplotype differs from all of the canonical haplotypes and all single-recombination recombinant canonical haplotypes would indicate an increased likelihood that an allele of said gene in said diploid subject harbors a genomic rearrangement.

15. The method of claim 13, wherein an increased likelihood that the chromosome region harbors a genomic deletion is predicted if the unphased genotypes can be reduced to a heterologous haplotype pair including (1) one haplotype identical to a canonical haplotype or single-recombination recombinant canonical haplotype, and (2) the other haplotype different from all of the canonical haplotypes and single-recombination recombinant canonical haplotypes, and different from one of the canonical haplotypes by one or more adjacent nucleotide variant markers.

16. A method for detecting an increased likelihood of a genomic rearrangement in an allele of a chromosome region of a diploid subject, said method comprising the steps of:
providing a haplotype collection comprising canonical haplotypes for the chromosome region representative of a defined heterogeneous subject population and single-recombination recombinant canonical haplotypes derived from said canonical haplotypes, each of said canonical haplotypes and single-recombination recombinant canonical haplotypes comprising a plurality of nucleotide variant markers;
providing unphased genotypes at said plurality of nucleotide variant markers in both alleles of said chromosome region in said diploid subject; and
comparing said unphased genotypes with the haplotypes in said haplotype collection, wherein an increased likelihood that the chromosome region harbors a genomic rearrangement is predicted if the unphased genotypes can be reduced to a heterologous haplotype pair including (1) one haplotype identical to a canonical haplotype or single-recombination recombinant canonical haplotype, and (2) another haplotype different from all of the canonical haplotypes and single-recombination recombinant canonical haplotypes, and different from one of the canonical haplotypes at one or more adjacent nucleotide variant markers.

17. A computer program product comprising a computer-usable medium having computer-readable program code embodied thereon for enabling a processor to assist in detecting an increased likelihood of a genomic rearrangement in an allele of a chromosome region of a diploid subject, said computer-readable program code effecting the following steps within a computing system:
providing a haplotype collection comprising canonical haplotypes and single-recombination recombinant canonical haplotypes for a chromosome region in a heterogeneous subject population, each of said canonical haplotypes and single-recombination recombinant canonical haplotypes comprising a plurality of nucleotide variant markers;
receiving unphased genotypes at said plurality of nucleotide variant markers in said chromosome region in said diploid subject; and
comparing said unphased genotypes with said canonical haplotypes and said single-recombination recombinant canonical haplotypes, wherein said computer-readable program code further effects the processor to indicate an increased likelihood that an allele of said chromosome region in said diploid subject harbors a genomic rearrangement when said unphased genotypes cannot be reduced to a pair of haplotypes formed by said canonical haplotypes and/or said single-recombination recombinant canonical haplotypes.

18. The computer program product of claim 17, wherein said diploid subject is a human.

19. The computer program product of claim 17, wherein said computer-readable program code enables the computer system to indicate an increased likelihood that an allele of said chromosome region in said diploid subject harbors a genomic rearrangement if:
the unphased genotypes suggest a heterologous haplotype pair including one haplotype identical to a first canonical haplotype or single-recombination recombinant canonical haplotype,
while the other haplotype is different from all of the canonical haplotypes and single-recombination recombinant canonical haplotypes, and differs from one of the canonical haplotypes by one or more adjacent nucleotide variant markers.

20. The computer program product of claim 17, wherein each of said canonical haplotypes are present in said heterogeneous subject population at a frequency of at least 1%.

21. The computer program product of claim 17, wherein each of said canonical haplotypes includes at least 8 nucleotide variant markers.

22. The computer program product of claim 17, wherein said unphased genotypes are determined by indiscriminative PCR amplification of both alleles of said chromosome region and DNA sequencing the amplified products.

23. The computer program product of claim 17, wherein said computer-readable program code further effects the processor to perform a step of providing a haplotype pair collection including pairs of haplotypes selected from the group consisting of said canonical haplotypes and said single-recombination recombinant canonical haplotypes, and wherein said computer-readable program code also enables the processor to compare the unphased genotypes with said pairs of haplotypes to determine whether one of said haplotype pairs matches the unphased genotypes.

24. The computer program product of claim 17, wherein said plurality of nucleotide variant markers are located within one gene.

25. A computer program product comprising a computer-usable medium having computer-readable program code embodied thereon for enabling a processor to assist in detecting an increased likelihood of a genomic deletion in an allele of a chromosome region of a diploid subject, said computer-readable program code effecting the following steps within a computing system:
providing canonical haplotypes for said gene in a heterogeneous subject population, each of said canonical haplotypes comprising at least 5 nucleotide variant markers within said gene;
providing single-recombination recombinant canonical haplotypes based on said canonical haplotypes;
generating a haplotype pair collection comprising pairs of haplotypes selected from the group consisting of said canonical haplotypes and said single-recombination recombinant canonical haplotypes;
receiving unphased genotypes at said at least 5 nucleotide variant markers in said gene of said diploid subject, wherein said unphased genotypes are determined by indiscriminative PCR amplification of both alleles of a portion of said gene and sequencing the amplified products; and comparing said unphased genotypes with said pairs of haplotypes, wherein said computer-readable program code enables the processor to indicate an increased likelihood that an allele of the gene harbors a genomic deletion if the unphased genotypes can be reduced to a heterologous haplotype pair including (1) one haplotype identical to a canonical haplotype or single-recombination recombinant canonical haplotype, and (2) the other haplotype different from all of the canonical haplotypes and single-recombination recombinant canonical haplotypes, and different from one of the canonical haplotypes by one or more adjacent nucleotide variant markers.

26. A computer program product comprising a computer-usable medium having computer-readable program code embodied thereon for enabling a processor to assist in detecting an increased likelihood of a genomic rearrangement in an allele of a chromosome region of a diploid subject, said computer-readable program code effecting the following steps within a computing system:

comparing unphased genotypes at a plurality of nucleotide variant markers in both alleles of said chromosome region in said diploid subject with canonical haplotypes within said chromosome region in a heterogeneous subject population, each of said canonical haplotypes comprising said plurality of nucleotide variant markers; and predicting, from said unphased genotypes, a pair of subject haplotypes that most resemble one or two members of said canonical haplotypes, wherein said computer-readable program code enables the processor to indicate an increased likelihood that an allele of said gene in said diploid subject harbors a genomic rearrangement if the subject haplotype pair includes one haplotype identical to a first canonical haplotype and the other haplotype differs from all of the canonical haplotypes.

27. The computer program product of claim 26, wherein said computer-readable program code further enables the processor to compare said unphased genotypes with single-recombination recombinant canonical haplotypes, wherein said computer-readable program code enables the processor to indicate an increased likelihood that an allele of said gene in said diploid subject harbors a genomic rearrangement if the subject haplotype pair includes one haplotype identical to a first canonical haplotype or single-recombination recombinant canonical haplotype, and the other haplotype differs from all of the canonical haplotypes and all single-recombination recombinant canonical haplotypes.

28. The computer program product of claim 27, wherein said computer-readable program code enables the processor to indicate an increased likelihood that the chromosome region harbors a genomic deletion if the unphased genotypes can be reduced to a heterologous haplotype pair including (1) one haplotype identical to a canonical haplotype or single-recombination recombinant canonical haplotype, and (2) the other haplotype different from all of the canonical haplotypes and single-recombination recombinant canonical haplotypes, and different from one of the canonical haplotypes by one or more adjacent nucleotide variant markers.

29. A computer program product comprising a computer-usable medium having computer-readable program code embodied thereon for enabling a processor to assist in detecting an increased likelihood of a genomic rearrangement in an allele of a chromosome region of a diploid subject, said computer-readable program code effecting the following steps within a computing system:

providing a haplotype collection comprising canonical haplotypes for the chromosome region representative of a defined heterogeneous subject population and single-recombination recombinant canonical haplotypes derived from said canonical haplotypes, each of said canonical haplotypes and single-recombination recombinant canonical haplotypes comprising a plurality of nucleotide variant markers;

providing unphased genotypes at said plurality of nucleotide variant markers in both alleles of said chromosome region in said diploid subject; and comparing said unphased genotypes with the haplotypes in said haplotype collection, wherein said computer-readable program code enables the processor to indicate an increased likelihood that the chromosome region harbors a genomic rearrangement if the unphased genotypes can be reduced to a heterologous haplotype pair including (1) one haplotype identical to a canonical haplotype or single-recombination recombinant canonical haplotype, and (2) another haplotype different from all of the canonical haplotypes and single-recombination recombinant canonical haplotypes, and different from one of the canonical haplotypes at one or more adjacent nucleotide variant markers.

30. A computer program product comprising a computer-usable medium having computer-readable program code embodied thereon for enabling a processor to assist in detecting an increased likelihood of a genomic rearrangement in an allele of a chromosome region of a diploid subject, said computer-readable program code effecting the following steps within a computing system:

receiving information on unphased genotypes at a plurality of nucleotide variant markers in both alleles of said chromosome region in said diploid subject; and comparing said unphased genotypes with canonical haplotypes within said chromosome region in a heterogeneous subject population and predicting, from said unphased genotypes, a pair of subject haplotypes that most resemble one or two members of said canonical haplotypes, wherein the fact that the subject haplotype pair includes one haplotype identical to a first canonical haplotype and the other haplotype differs from all of the canonical haplotypes would indicate an increased likelihood that an allele of said gene in said diploid subject harbors a genomic rearrangement.

31. The computer program product of claim 30, wherein said computer program product further enables the processor to receive information representative of said canonical haplotypes within said chromosome region in a heterogeneous subject population.

32. A system for detecting an increased likelihood of a genomic rearrangement in an allele of a chromosome region of a diploid subject, comprising:

a first interface module for receiving information representative of unphased genotypes at a plurality of nucleotide variant markers in both alleles of said chromosome region in said diploid subject;

a second interface module for providing information representative of a haplotype collection comprising canonical haplotypes and single-recombination recombinant canonical haplotypes for the chromosome region in a heterogeneous subject population, each of said canonical haplotypes and single-recombination recombinant canonical haplotypes comprising said plurality of nucleotide variant markers;

computer program means for comparing said unphased genotypes with said canonical haplotypes to determine whether said unphased genotypes can be reduced to a pair of haplotypes formed by said canonical haplotypes and/or said single-recombination recombinant canonical haplotypes; and computer program means for enabling the system to indicate an increased likelihood that an allele of said chromosome region in said diploid subject harbors a genomic rearrangement when said unphased genotypes cannot be reduced to a pair of haplotypes formed by said canonical haplotypes and/or said single-recombination recombinant canonical haplotypes.

33. A method for producing a transmittable data product characterizing the presence or absence of an increased likelihood of a genomic rearrangement in an allele of a chromosome region of a diploid subject, said method comprising the steps of:

providing a haplotype collection comprising canonical haplotypes and single-recombination recombinant canonical haplotypes for a chromosome region in a heterogeneous subject population, each of said canonical haplotypes and single-recombination recombinant canonical haplotypes comprising a plurality of nucleotide variant markers;

providing unphased genotypes at said plurality of nucleotide variant markers in said chromosome region in said diploid subject; and comparing said unphased genotypes with said canonical haplotypes and said single-recombination recombinant canonical haplotypes, wherein the fact that said unphased genotypes cannot be reduced to a pair of haplotypes formed by said canonical haplotypes and/or said single-recombination recombinant canonical haplotypes would indicate an increased likelihood that an allele of said chromosome region in said diploid subject harbors a genomic rearrangement; and casting the result in said comparing step into a transmittable data product.

* * * * *